United States Patent
Paroth et al.

(10) Patent No.: US 10,687,881 B2
(45) Date of Patent: Jun. 23, 2020

(54) SURGICAL INSTRUMENT

(71) Applicant: Z-Medical GmbH & Co. KG, Tuttlingen (DE)

(72) Inventors: Christel Paroth, Tuttlingen (DE); Alexander Henninger, Muhlheim (DE); Zbigniew Combrowski, Tuttlingen (DE)

(73) Assignee: Z-Medical GmbH & Co. KG, Tuttlingen (DE)

( * ) Notice: Subject to any disclaimer, the term of this patent is extended or adjusted under 35 U.S.C. 154(b) by 911 days.

(21) Appl. No.: 14/501,788

(22) Filed: Sep. 30, 2014

(65) Prior Publication Data

US 2015/0094781 A1 Apr. 2, 2015

(30) Foreign Application Priority Data

Sep. 30, 2013 (DE) .................. 10 2013 110 796

(51) Int. Cl.
*A61B 17/58* (2006.01)
*A61B 17/88* (2006.01)
*A61B 17/86* (2006.01)
*A61B 17/70* (2006.01)
*A61B 90/00* (2016.01)

(52) U.S. Cl.
CPC ...... *A61B 17/8863* (2013.01); *A61B 17/7074* (2013.01); *A61B 17/7091* (2013.01); *A61B 17/8605* (2013.01); *A61B 17/7032* (2013.01); *A61B 2090/037* (2016.02)

(58) Field of Classification Search
CPC ............ A61B 17/7032; A61B 17/8875; A61B 17/8894; A61B 17/8877; A61B 17/888; A61B 17/7074; A61B 17/7091; A61B 17/8605; A61B 17/8863; A61B 17/8886; A61B 17/8888; A61B 17/8891; A61B 2090/037; A61B 2019/307; B25B 15/001; B25B 15/02; B25B 23/101; B25B 23/105; B25B 23/141; B25B 23/1415; B25B 23/142
USPC ................ 606/86 R, 99–100, 104, 246–279, 606/300–321, 86 A, 86 B; 81/451, 471
See application file for complete search history.

(56) References Cited

U.S. PATENT DOCUMENTS

| 5,464,407 A * | 11/1995 | McGuire ................ A61B 17/15 606/104 |
| 6,723,099 B1 | 4/2004 | Goshert |
| 2005/0120836 A1 * | 6/2005 | Anderson ........... B25B 23/0035 81/73 |
| 2008/0045953 A1 | 2/2008 | Garamszegi |
| 2009/0012571 A1 * | 1/2009 | Perrow .............. A61B 17/1671 606/280 |

(Continued)

FOREIGN PATENT DOCUMENTS

| EP | 1552794 A2 | 7/2005 |
| EP | 1882451 A2 | 1/2008 |

(Continued)

*Primary Examiner* — Jessica Weiss
(74) *Attorney, Agent, or Firm* — Fishman Stewart PLLC

(57) ABSTRACT

A surgical instrument for separating an introducer sheath from a device connected to the introducer sheath is disclosed. In embodiments, the surgical instrument includes an extension extending in a longitudinal direction; a pin; and a separator connecting the extension and the pin.

15 Claims, 5 Drawing Sheets

(56) References Cited

U.S. PATENT DOCUMENTS

| | | | |
|---|---|---|---|
| 2009/0228052 A1* | 9/2009 | Beardsley | A61B 17/7032 606/305 |
| 2010/0155453 A1 | 6/2010 | Bombard et al. | |
| 2011/0040335 A1* | 2/2011 | Stihl | A61B 17/7032 606/302 |
| 2012/0109224 A1 | 5/2012 | Biedermann et al. | |
| 2012/0323278 A1* | 12/2012 | Tsuang | A61B 17/1671 606/264 |
| 2013/0090691 A1* | 4/2013 | Zhang | A61B 17/7001 606/264 |
| 2013/0103095 A1* | 4/2013 | Brumfield | A61B 17/7064 606/279 |
| 2013/0172920 A1* | 7/2013 | Euteneuer | A61B 17/88 606/185 |

FOREIGN PATENT DOCUMENTS

| | | |
|---|---|---|
| FR | 2731610 A1 | 9/1996 |
| WO | 03030746 A1 | 4/2003 |

\* cited by examiner

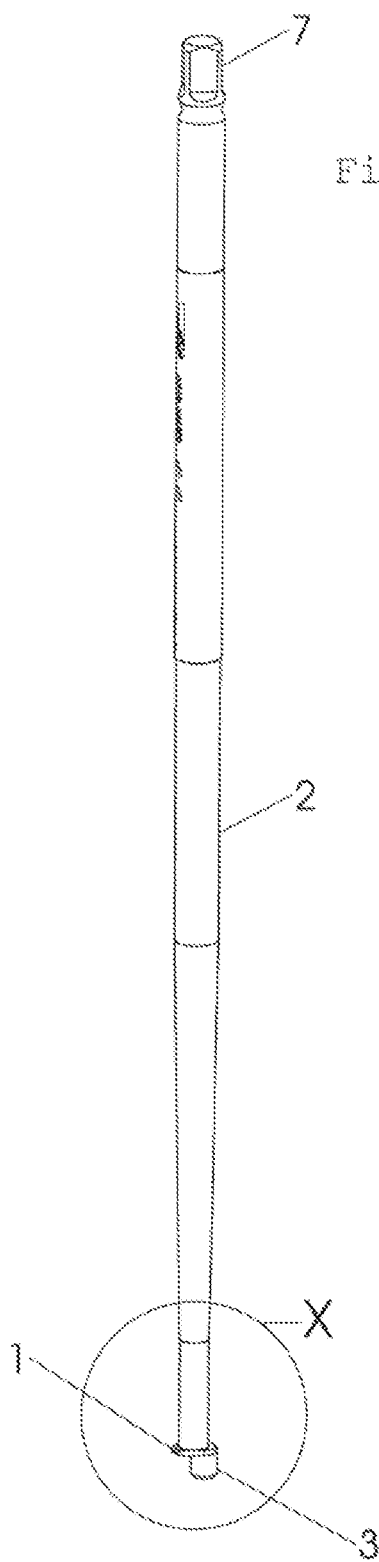
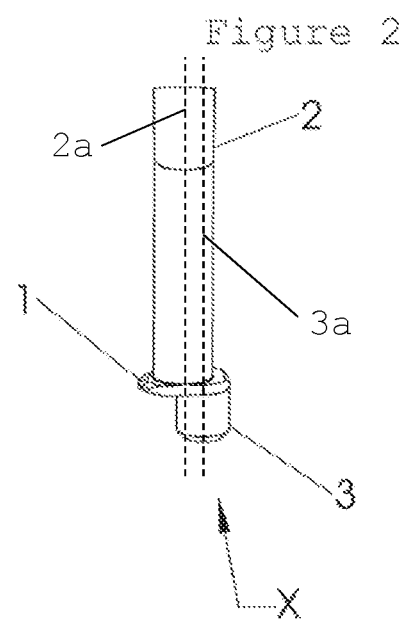
Figure 1
Figure 2

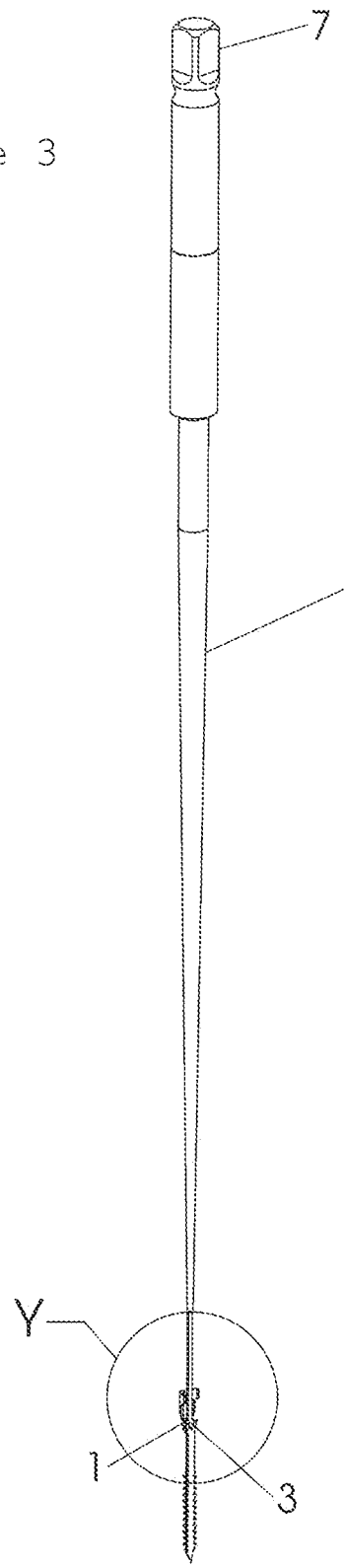
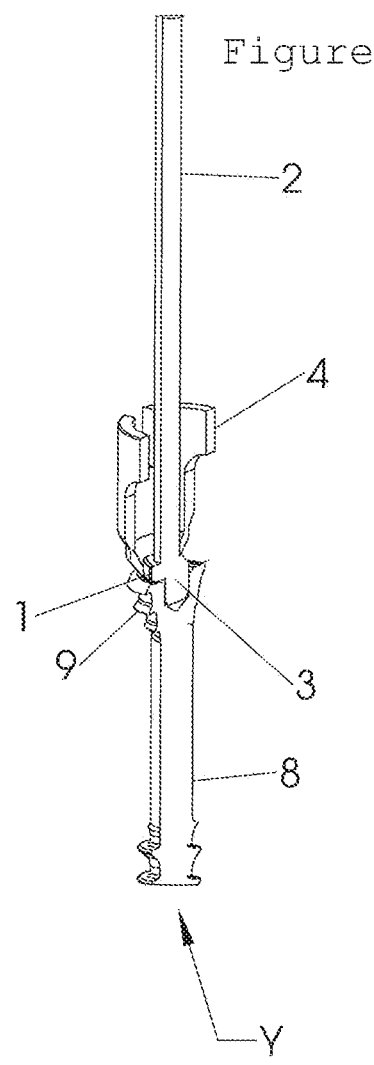

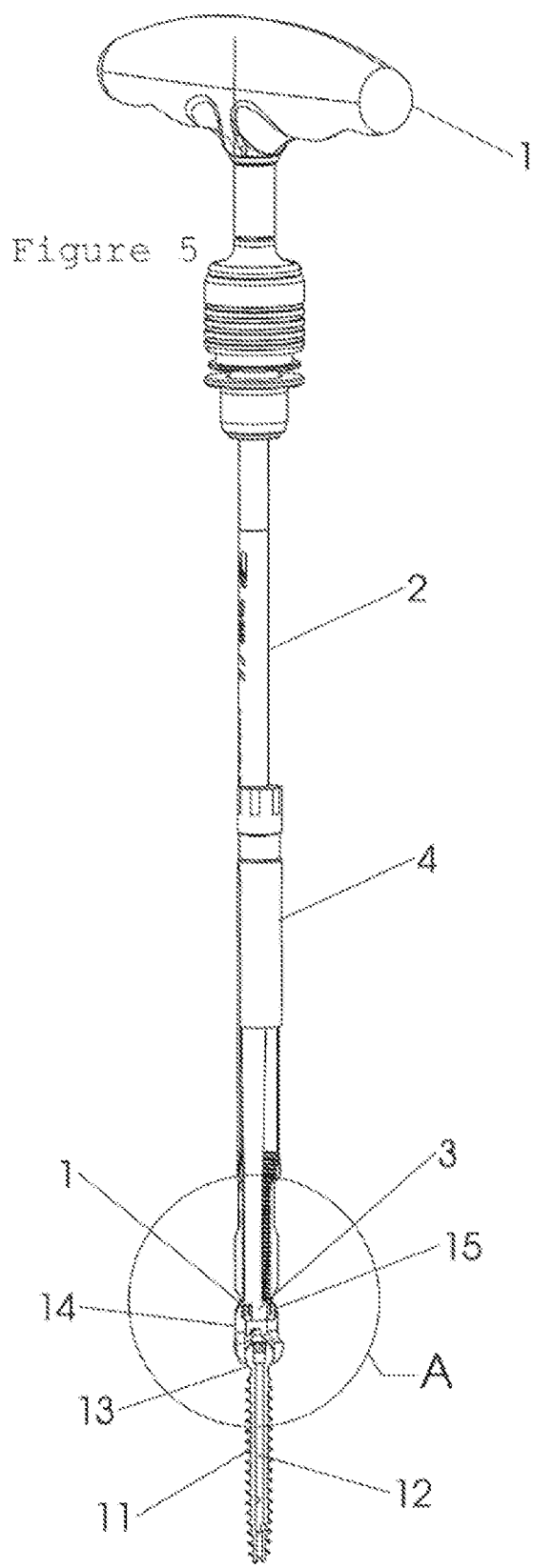
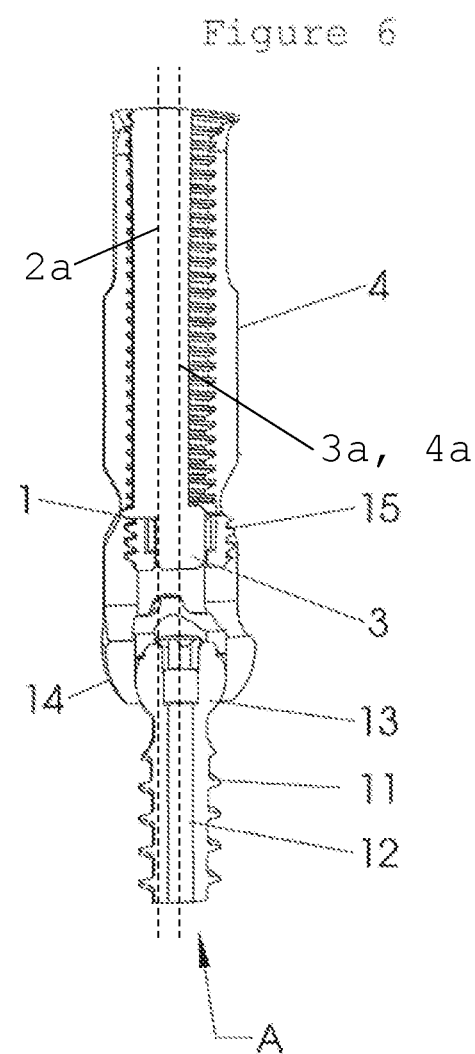

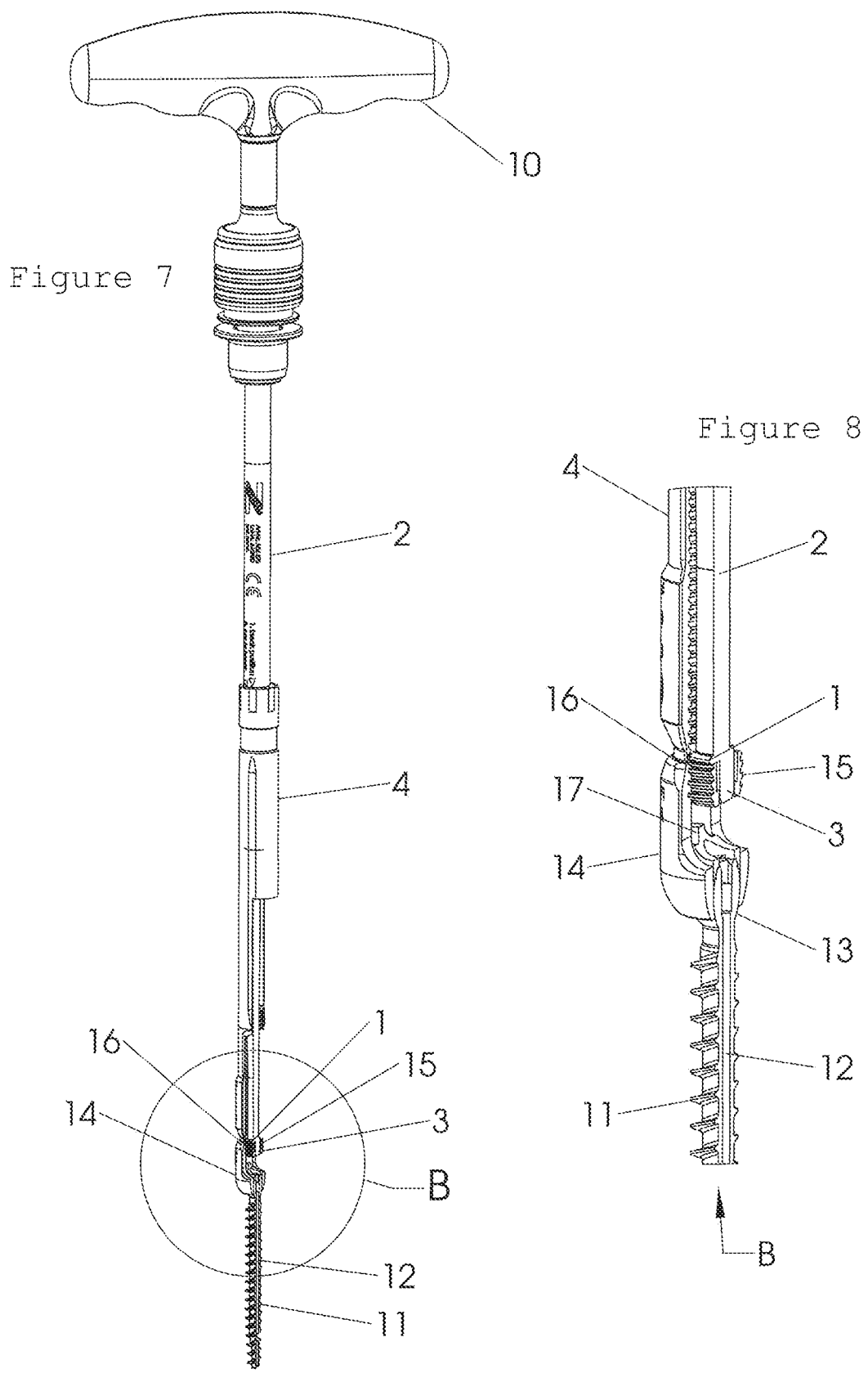

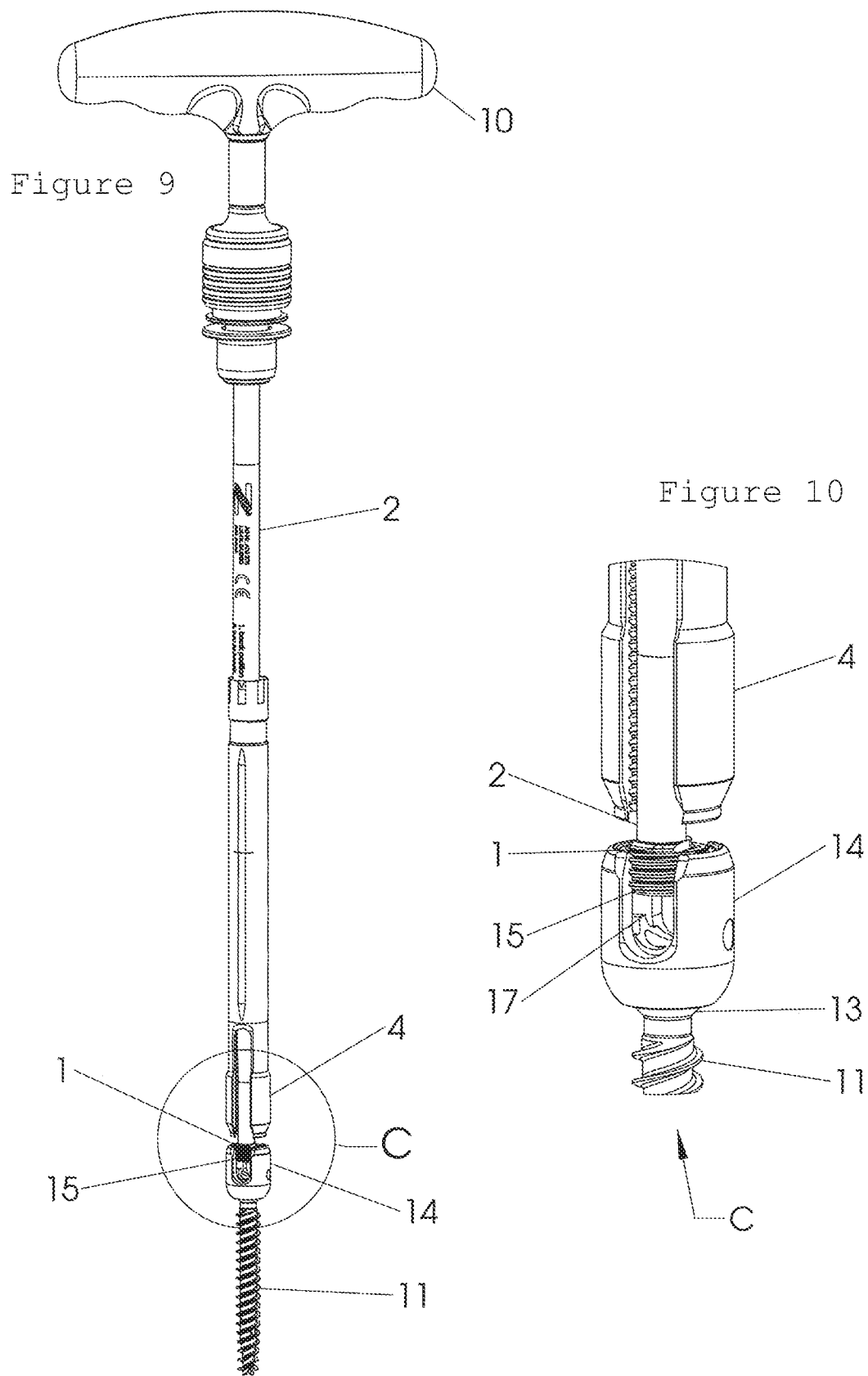

SURGICAL INSTRUMENT

CROSS-REFERENCE TO RELATED APPLICATION

This application claims the benefit of priority to German patent application No. 102013110796.6, filed Sep. 30, 2013, which is incorporated herein by reference in its entirety as though fully set forth herein.

TECHNICAL FIELD

The present invention relates to a surgical instrument.

BACKGROUND

Surgery involves the use of implants such as cages, screws and similar instruments. These implants are particularly relevant for spinal surgery.

Such implants continue to be produced with more and more of an extension, such as a shaft, holding or driving instruments and a handle, wherein the extension is connected to the implant by means of a joint such as a pre-determined breaking point.

The task of the pre-determined breaking point is to hold the implant and extension in a rigid position until it reaches the intended position.

According to the designs of most manufacturers, the extension is broken off by breaking the extension into several, usually two, parts using additional appropriate instruments Ultimately, the extension is broken off from the implant by levering motions. This action results in harmful chips and splinters that in themselves can increase the risk of infection. According to the designs of most manufacturers, the extension is broken off by breaking the extension into several, usually two, parts using additional appropriate instruments.

BRIEF SUMMARY

The purpose of the invention is to provide a clean breaking point that is as smooth and angle-free as possible and to enable the breaking off to take place with no splintering and little effort. The invention should also prevent crushing or distending the surrounding tissue due to the levering motions.

The invention relates to a surgical instrument for breaking off a driver tool sleeve connected to a device with an introducer sheath; the instrument is configured such that the introducer sheath is connected to the medical device at a pre-determined breaking point. For example, this is the design used in pedicle screws. In that case, pedicle screws are inserted into vertebrae using a pedicle. The introducer sheath in this minimally-invasive procedure is used to extend a tulip head. The tulip head is a connected adaptor piece between the pedicle screw and the extender piece. For example, the tulip head can house a bar that connects and fixes various pedicle screws within the body.

For this purpose, the Ini has, for example, a recessed cross-slot head for a screwing tool on the side facing away from the bar. This allows the Ini to be screwed into the recess of the tulip head through the introducer sheath using a screwing device, in order to set in a bar inserted there.

The introducer sheath of this invention is configured such that it can be connected directly to the tulip head or to another part, such as the screw head. For this purpose, the introducer sheath is cylindrical and hollow, such that other tools, such as the screwing device, can be inserted into the introducer sheath, for example to be able to screw the device connected at the end of the introducer sheath into the bone. The device specified for this invention may be a cage, a screw, in particular a bone screw or other implant, or an intra- and/or extracorporeal extension of an implant.

The invention relates to a surgical instrument with an extension with a separator. In this case, the extension is a bar element that is either hollow or full. The bar element can be either linear or bent or flexible. Ultimately, it is only important that the bar element is used to bring the separator to the region of the introducer sheath where the device connected to the introducer sheath is to be broken off from the introducer sheath.

The separator can be either a lip or cam. In this respect it is preferable if the separator can be arranged on the extension. It is only essential that when used as intended, the separator is brought into the region of the introducer sheath where there is, for example, a pre-determined breaking point between the introducer sheath and the device connected to the introducer sheath.

The separator is preferably configured at least partially with a curve, wherein it can have a cutting edge. For this purpose, it is advantageous if the cutting edge is sharp. However, it does not require a sharpened cutting edge to carry out the cutting action.

It is conceivable that the extension with the separator is configured as a single piece or as multiple pieces. In the case of a single-piece design for the extension with the separator, there are different types of surgical instruments depending on the introducer sheath and device. However, it is also conceivable that the separator can be connected to the extension with a screw connection, for example. In that case, the extension and the separator may be separate; i.e., they are configured as more than one piece.

In this way, it would be possible, for example, that different types of separators could be screwed onto the same extension. Other possible connections besides the screw connector of the separator are also conceivable, as long as the connection is reversible and different types of separators could be screwed onto the same extension.

It is also conceivable that the surgical instrument is a combination instrument that fulfills several functions, such as both screwing and separating.

In one example of this invention, the extension has a coupling to hold a handle. The coupling in this case is at the opposite end of the extension from the separator. After the handle has been attached to the coupling, the separator can be brought into a favorable rotated movement or position by twisting the extension, for example, so that the separator can execute a cutting, peeling or pressing function by means of its curved shape and therein separates the introducer sheath from the medical device. The separation can be done by hand using the instrument or by a suitable driver.

The extension is configured so that the extension can be inserted into the introducer sheath. However, it is also conceivable that the extension is configured so that it can be placed upon the introducer sheath. For this purpose, the extension may be able to be spread apart by means of slits in order to place it on the introducer sheath and to introduce the separator to the respective pre-determined breaking point from the outside. In this case, the outside refers to the region that is not a part of the interior of the introducer sheath.

The surgical instrument is configured so that the separator extends out from the extension. For this purpose, the separator is configured as a cam or a lip, for example as a part of a circle or a point extending out from the area; typically, this would be extending out perpendicularly.

Further, the separator is configured such that separation of the introducer sheath from the tulip head of an implant or from an implant is ensured. For this purpose, the separator has both a pin and the extension. The pin can be eccentrically positioned, for example, or positioned from the centered or partially centered. The position is relative to the extension. If the pin is positioned from the center, the pin represents a linear continuation of the extension. If the pin is position eccentrically, the pin is not a linear continuation, but is a broken continuation. For this purpose, the pin is configured so that it can be inserted into a part of the device, wherein the device serves as a counter bearing to the rotation. For this purpose, the part may be, for example, a screw head or a tulip head and/or an Ini that is inserted into the tulip head. The pin can therefore be inserted with a non-positive connection into the Ini, the tulip head or the screw head. However, a positive-fit connection is also conceivable. It is not imperative that there is a non-positive connection. Ultimately, a design like the present invention is also possible, wherein the pin can be avoided completely.

The pin serves as the counter bearing to rotation. This means that a rotation or twisting movement of the extension into the introducer sheath is possible. For this purpose, the pin may be mounted so that it can rotate freely or so that is rotates with the Ini, for example. The decision is left up to the judgment of the specialist or can be adapted to the needs of the user.

A position via a connection to the shaft behind the separator would also be conceivable.

BRIEF DESCRIPTION OF THE DRAWINGS

FIG. 1 is an isometric side view of the surgical instrument according to an embodiment of the invention;

FIG. 2 is an enlarged view of a section of FIG. 1;

FIG. 3 is an isometric view of another example of a surgical instrument according to another embodiment of the invention;

FIG. 4 is an enlarged view of a section of FIG. 3;

FIG. 5 is an isometric view of a surgical instrument according to another embodiment of the invention;

FIG. 6 is an enlarged detailed view of a section of FIG. 5;

FIG. 7 is a partially cut isometric view of a surgical instrument according to another embodiment of the invention;

FIG. 8 is an enlarged view of a section of FIG. 7;

FIG. 9 is an isometric view of a surgical instrument according to another embodiment of the invention;

FIG. 10 is an enlarged detailed view of a section of FIG. 9.

DETAILED DESCRIPTION

FIG. 1 depicts a surgical instrument. The surgical instrument is comprised of an extension 2 and an eccentrically positioned pin 3, which is characterized by a separator 1 as a connecting piece. On the opposite end from the separator 1, the extension 2 has a coupling 7. FIG. 1 also depicts an enlarged section X. The enlarged area X is presented in FIG. 2. This view illustrates how the pin 3 is positioned as an uninterrupted continuation of the extension 2 and how the separator 1 forms a partially circular cutting edge between the pin 3 and the extension 2.

Additional statements and details for FIGS. 3 to 10 are to be interpreted such that the same reference numbers correspond to the same features. Any statements made with respect to a reference number and its corresponding feature apply to the remaining figures as well.

FIG. 3 depicts the extension 2 with its associated coupling 7. At the end opposite end the coupling 7, the extension 2 again forms a pin 3 and a separator 1. FIG. 3 also contains an enlarged area Y that is shown in enlarge detail in FIG. 4. The partially cross-sectioned view in FIG. 4 illustrates how the pin 3 is engaged within a bone screw 8. For this purpose, the pin 3 can be connected by means of a positive or non-positive locking connection to the bone screw.

The difference between a positive or non-positive locking connection is that the bone screw 8 makes the rotating movement along with the pin 3 when there is a non-positive locking connection. When there is a positive locking connection, the pin 3 can rotate freely in a screw head 9 without the bone screw 8 reproducing the rotation of the extension 2. Moreover, the introducer sheath 4 is shown, in this case with a shorter design compared to FIG. 5. An extension 2 may include a longitudinal axis 2a. A pin 3 may include a longitudinal axis 3a. An introducer sheath 4 may include a longitudinal axis 4a.

The separator 1 can break off the introducer sheath 4 within the screw head using an eccentrically positioned pin 3. For this purpose, the extension 2 is rotated about its axis. This rotation results in the separator 1 being guided along the upper length of the screw head 9 and thereby separates the introducer sheath 4 from the screw head 9 in a defined motion, wherein the introducer sheath 4 is connected to the screw head 9 at a pre-defined breaking point.

FIG. 5 depicts how the extension 2 is inserted into the introducer sheath 4. It also shows a handle 10 that is positioned on the coupling 7 that can no longer be seen. The handle 10 is connected to the extension 2 such that any rotational movement of the handle 10 also produces a rotation of the extension 2. A portion of FIG. 5 is shown in cross-section. FIG. 5 also shows a pedicle screw 11, wherein the pedicle screw 11 has a cannulation 12 and a pedicle screw head 13. The pedicle screw head 13 is configured specifically to be moveable within a tulip head 14. Moreover, an Ini 15 is screwed into the tulip head 14; the Ini 15 in turn has a pin 3 inserted in it, which has the separator 1. An Ini 15 may include an adjusting screw that may include external threads, a body, and an aperture that may extend through the body. An Ini 15 may include a recessed cross-slot head for a screwing tool on the side facing away from the bar. This may allow the Ini 15 to be screwed into the recess of the tulip head 14 through the introducer sheath 4 using a screwing device, such as in order to set in a bar inserted there.

FIG. 6 depicts the region of FIG. 5 designated as A in an enlarged view. This view readily shows how the pin 3 is inserted into the Ini 15 and how the separator 1 is configured such that separation of the introducer sheath 4 from the tulip head 14 is accomplished.

FIG. 7 again depicts how the extension 2 is connected to the handle 10 via the coupling 7, which is not visible. The extension 2 extends into the introducer sheath 4. A portion of FIG. 7 is shown in cross-section.

A region B is also depicted, of which an enlarged view is provided by FIG. 8. FIG. 8 readily shows how the pin 3 of the extension 2 is inserted into the Ini 15 within the introducer sheath 4. Moreover, it is clear how the separator 1 is positioned against a pre-determined breaking point 16. It is also shown how the tulip head 14 has an opening 17 to accommodate a bar. When connecting to another pedicle screw 11, the opening 17 can be used such that a bar, typically positioned perpendicular to the pedicle screw 11, reaches through the opening 17 in the tulip head 14 and extends as far as another pedicle screw 11 connected to it. Ultimately, the bar can be fixed in place by tightening the Ini 15 within the opening 17 of the tulip head 14.

FIGS. 9 and 10 depict how the introducer sheath 4 is separated from the tulip head 14 by a 360° rotation of the separator 1 at the pre-determined breaking point 16. FIG. 10 is an enlarged view of region C in FIG. 9.

The invention claimed is:

1. A surgical instrument for separating an introducer sheath from a device connected to the introducer sheath, the surgical instrument comprising:
   an extension extending in a longitudinal direction;
   a pin, the pin including a cylindrical configuration; and
   a separator connecting the extension and the pin, the separator including a substantially planar configuration, the separator comprising a cam or a cutting edge;
   wherein the pin is positioned eccentrically with respect to the extension; wherein the pin is configured to be inserted into a part of said device;
   wherein during use, said device is configured to serve as a counter bearing to rotation;
   wherein a longitudinal axis of the extension is configured to be positioned eccentrically with respect to a longitudinal axis of said introducer sheath; and wherein a longitudinal axis of the pin and the longitudinal axis of said introducer sheath are configured to be common such that the pin is positioned concentrically with respect to said introducer sheath.

2. The surgical instrument of claim 1, wherein the separator comprises a lip.

3. The surgical instrument of claim 1, wherein the cutting edge is tapered such that a thickness of the separator tapers in a radial direction; wherein a minimum of the thickness of the separator is at the cutting edge; and the cutting edge is disposed at an outer portion of the separator.

4. The surgical instrument of claim 1, wherein the pin is positioned opposite from the cam or the cutting edge of the separator with respect to the extension.

5. The surgical instrument of claim 1, wherein the extension is a linear bar element.

6. The surgical instrument of claim 1, further including a coupling configured to connect to a handle.

7. The surgical instrument of claim 1, wherein the longitudinal axis of the extension is positioned eccentrically with respect to the longitudinal axis of the pin.

8. A surgical assembly, including:
   the surgical instrument of claim 1, and
   the introducer sheath;
   wherein the extension is disposed in the introducer sheath such that the longitudinal axis of the extension is positioned eccentrically with respect to the longitudinal axis of the introducer sheath.

9. A surgical assembly, including:
   the surgical instrument of claim 1, and
   the device.

10. The surgical assembly of claim 9, wherein the pin of the surgical instrument is connected to the device by a non-positive locking connection.

11. The surgical assembly of claim 9, wherein the device is a bone screw.

12. The surgical assembly of claim 9, wherein said device includes a screw head or tulip head, and wherein the pin of the surgical instrument is configured for insertion into or connection with said screw head or tulip head.

13. The surgical assembly of claim 9, wherein the longitudinal axis of the extension of the surgical instrument is parallel to the longitudinal axis of the pin of the surgical instrument and a longitudinal axis of said device.

14. A surgical instrument for separating an introducer sheath from a device connected to the introducer sheath, the surgical instrument comprising:
   an extension extending in a longitudinal direction;
   a pin, the pin including a cylindrical configuration; and
   a separator connecting the extension and the pin, the separator including a substantially planar configuration;
   wherein the pin is positioned eccentrically with respect to the extension; wherein the pin is configured to be inserted into a part of said device;
   wherein during use, said device is configured to serve as a counter bearing to rotation;
   wherein a longitudinal axis of the extension is configured to be positioned eccentrically with respect to a longitudinal axis of said introducer sheath; wherein a longitudinal axis of the pin and the longitudinal axis of said introducer sheath are configured to be common such that the pin is positioned concentrically with respect to said introducer sheath; and wherein
   wherein the extension and the separator are formed as a single unitary piece.

15. The surgical instrument of claim 14, wherein the longitudinal axis of the extension is parallel to the longitudinal axis of the pin.

* * * * *